(12) United States Patent
Chang

(10) Patent No.: US 7,179,233 B2
Chang
(45) Date of Patent: Feb. 20, 2007

(54) COMPACT STRUCTURE OF A NEW BIOSENSOR MONITOR

(76) Inventor: Yu-Hong Chang, P.O. Box No. 6-57, Junghe, Taipei 235 (TW)

( * ) Notice: Subject to any disclaimer, the term of this patent is extended or adjusted under 35 U.S.C. 154(b) by 349 days.

(21) Appl. No.: 10/697,303

(22) Filed: Oct. 31, 2003

(65) Prior Publication Data

US 2005/0096565 A1    May 5, 2005

(51) Int. Cl.
*A61B 5/00* (2006.01)
*B65D 81/00* (2006.01)

(52) U.S. Cl. ............... 600/584; 600/573; 600/583

(58) Field of Classification Search ........ 600/573–584, 600/316, 347, 365; 606/181; 435/14; 422/99
See application file for complete search history.

(56) References Cited

U.S. PATENT DOCUMENTS

| | | | | |
|---|---|---|---|---|
| 5,035,704 | A | * | 7/1991 | Lambert et al. ............ 606/182 |
| 5,108,889 | A | * | 4/1992 | Smith et al. .................... 435/4 |
| 5,279,294 | A | * | 1/1994 | Anderson et al. ........... 600/322 |
| 5,504,011 | A | * | 4/1996 | Gavin et al. .................. 436/69 |
| 5,593,390 | A | * | 1/1997 | Castellano et al. ......... 604/187 |
| 5,951,492 | A | * | 9/1999 | Douglas et al. ............. 600/583 |
| 6,197,040 | B1 | * | 3/2001 | LeVaughn et al. .......... 606/182 |
| 6,261,245 | B1 | * | 7/2001 | Kawai et al. ................ 600/576 |
| 6,306,104 | B1 | * | 10/2001 | Cunningham et al. ....... 600/573 |
| 6,561,989 | B2 | * | 5/2003 | Whitson ...................... 600/573 |
| 6,966,880 | B2 | * | 11/2005 | Boecker et al. ............. 600/583 |
| 2002/0187076 | A1 | * | 12/2002 | DiCesare et al. ............. 422/99 |

* cited by examiner

*Primary Examiner*—Max F. Hindenburg
*Assistant Examiner*—Rene Towa
(74) *Attorney, Agent, or Firm*—Troxell Law Office PLLC

(57) ABSTRACT

The invention discloses a biosensor monitor with a housing to accommodate a printed circuit board for data analysis from the electrochemical reaction on the test strip, a lancing device for blood inoculation which requires only one finger to activate the release of a lancet. This new monitor includes a biosensor monitor and the lancing device to make it more compact in size.

2 Claims, 7 Drawing Sheets

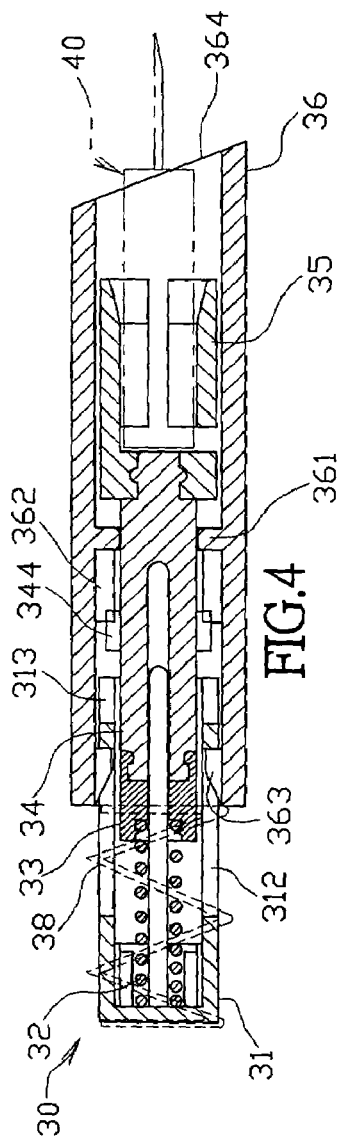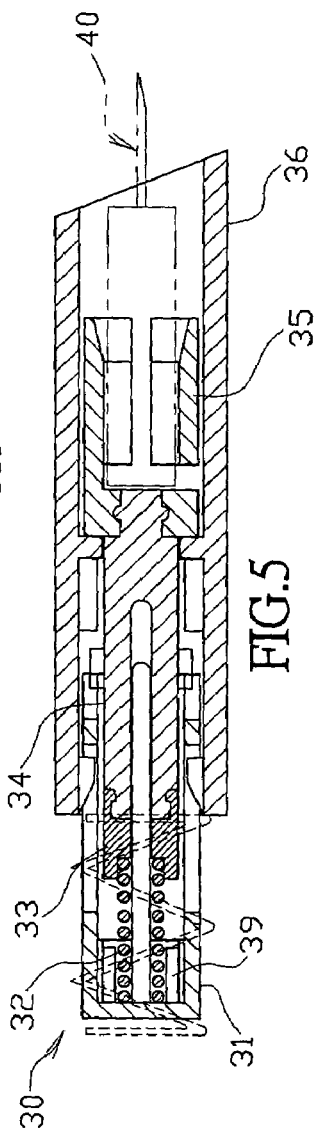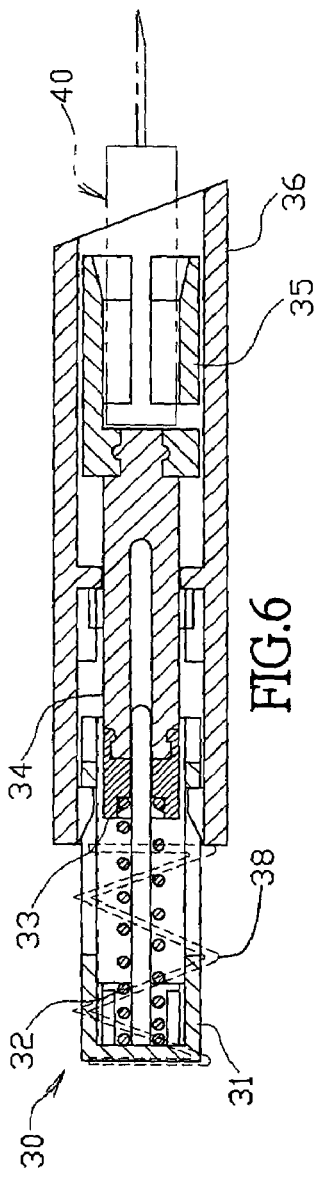

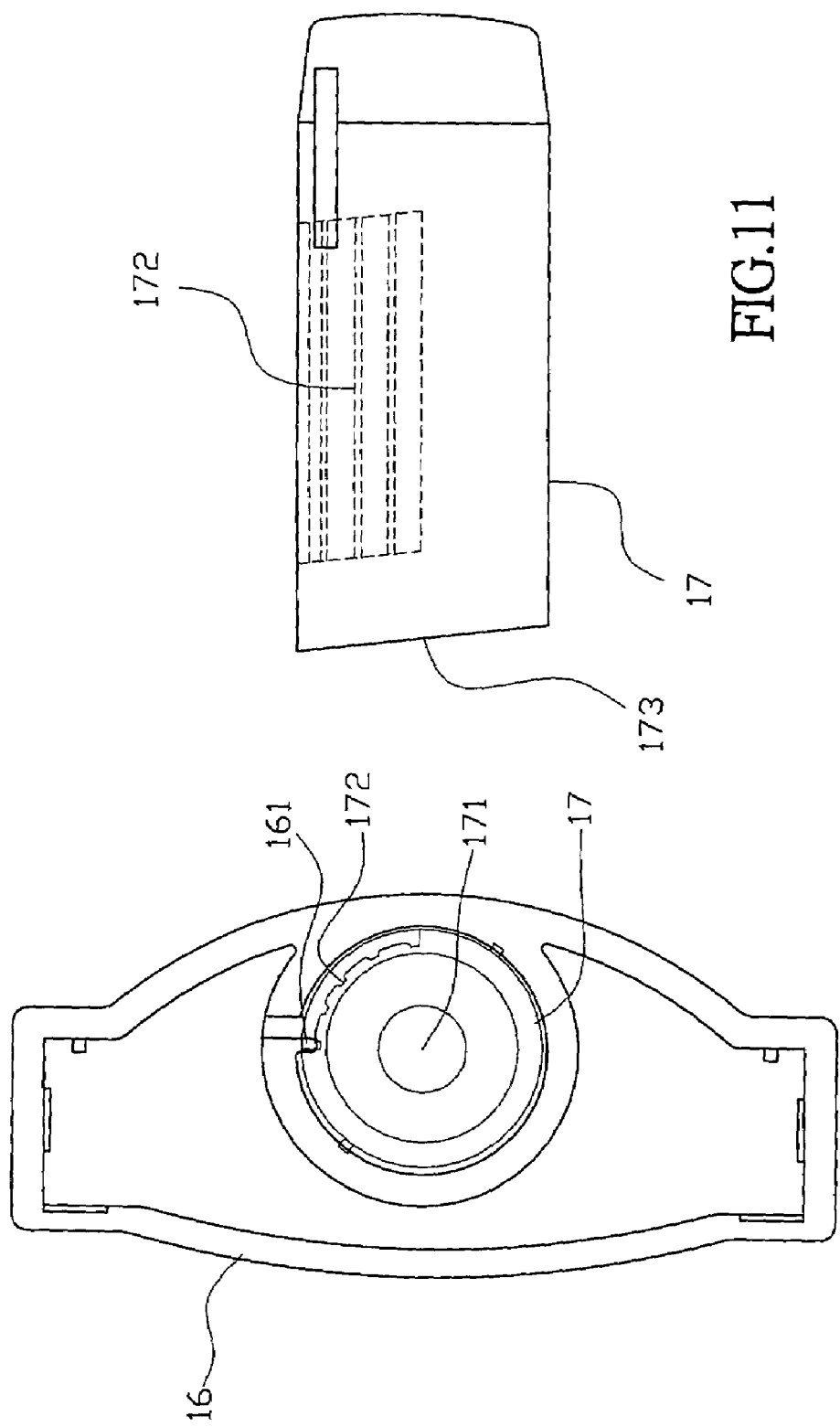

COMPACT STRUCTURE OF A NEW BIOSENSOR MONITOR

BACKGROUND OF THE INVENTION (a) Field of the Invention

This invention discloses the design of a biosensor monitor with a built-in lancing device for the convenience of the diabetic patients.

(b) Description of the Prior Art

All diabetic patients generally require a glucose monitor and a lancing device. Although both are portable, however, it requires more box space to put in both the monitor and blood lancer, making it rather bulky and inconvenient to carry around. Sometimes the lancing device is not present or lost, when it is time to perform a glucose measurement. Furthermore, to use a conventional lancing device requires two hands, one hand for triggering the lancing device to prick onto the fingertip of the other hand. Such conventional design of the monitor and the lancing device means two separate individual items, resulting in higher costs and packaging space. Moreover, the blood collection process by such lancing device with both hands is rather in inconvenient. Therefore, a new monitor with built-in lancing device to reduce cost and space to pack will be great niche for diabetics so that they won't leave home without the lancing device.

SUMMARY OF THE INVENTION

It is therefore the objective of this new design to provide a mechanism with the monitor and blood lancer in one piece, small in size and only one finger to operate, which will be free from the inconvenience and d drawbacks associated with the conventional biosensor device.

The mechanical structure of this monitor within which there is a circuit board with a receiver slot for the test strip to be inserted in. Signals received from the reaction of the reagent on the test strip with the applied blood will be analyzed via the built-in CPU (Central Processing Unit) and shown on the LCD (Liquid Crystal Display) screen and, or, be transmitted through the communication port (USB, Serial or Parallel Port) to the computer for data acquisition and analysis. This monitor also houses a lancing device, which composes of a number of parts and springs, to pierce the needle of the lancet into the skin for a tiny drop of blood. This lancing device can be installed a disposable lance. Replacing the used needle with a new one automatically reloads the lancing device ready to be triggered for blood inoculation, upon the touch one finger only. With this structural design, blood specimen can be easily collected with the touch of, say, a finger onto the lancing device to trigger the release of the lancet, and be applied onto the reagent of the test strip to determine the results of its electrochemical reaction through the measurement of electrical current or voltage which will then be processed via the built-in CPU to display on the LCD screen.

BRIEF DESCRIPTION OF THE DRAWINGS

The structure of the present invention may be more readily understood by one skilled in the art with reference to the following detailed drawings, wherein like elements are designated by identical reference numbers throughout the several views, and in which:

FIG. 4 is the cross-sectional view of the components of the lancing device when the needle is in the free, unloaded state.

FIG. 5 is the cross-sectional view of the several components of the lancing device when the lancing device is loaded and ready to trigger for the release of the lancet.

FIG. 6 is the cross-sectional view of the components of the lancing device is triggered and the lancet is released to its most forward position.

FIG. 10 is the top sectional view of the relative position of the protective cap and the lancet cover, showing the mechanism for the adjustment of the protective cap for different depth of lancet inoculated into the skin for different amount of blood drop.

FIG. 11 is the side view of the protective cap, showing the way to fix the lancet cover in different position for different depth of penetration into the skin.

DETAILED DESCRIPTION OF THE PREFERRED EMBODIMENTS

Figure 1:
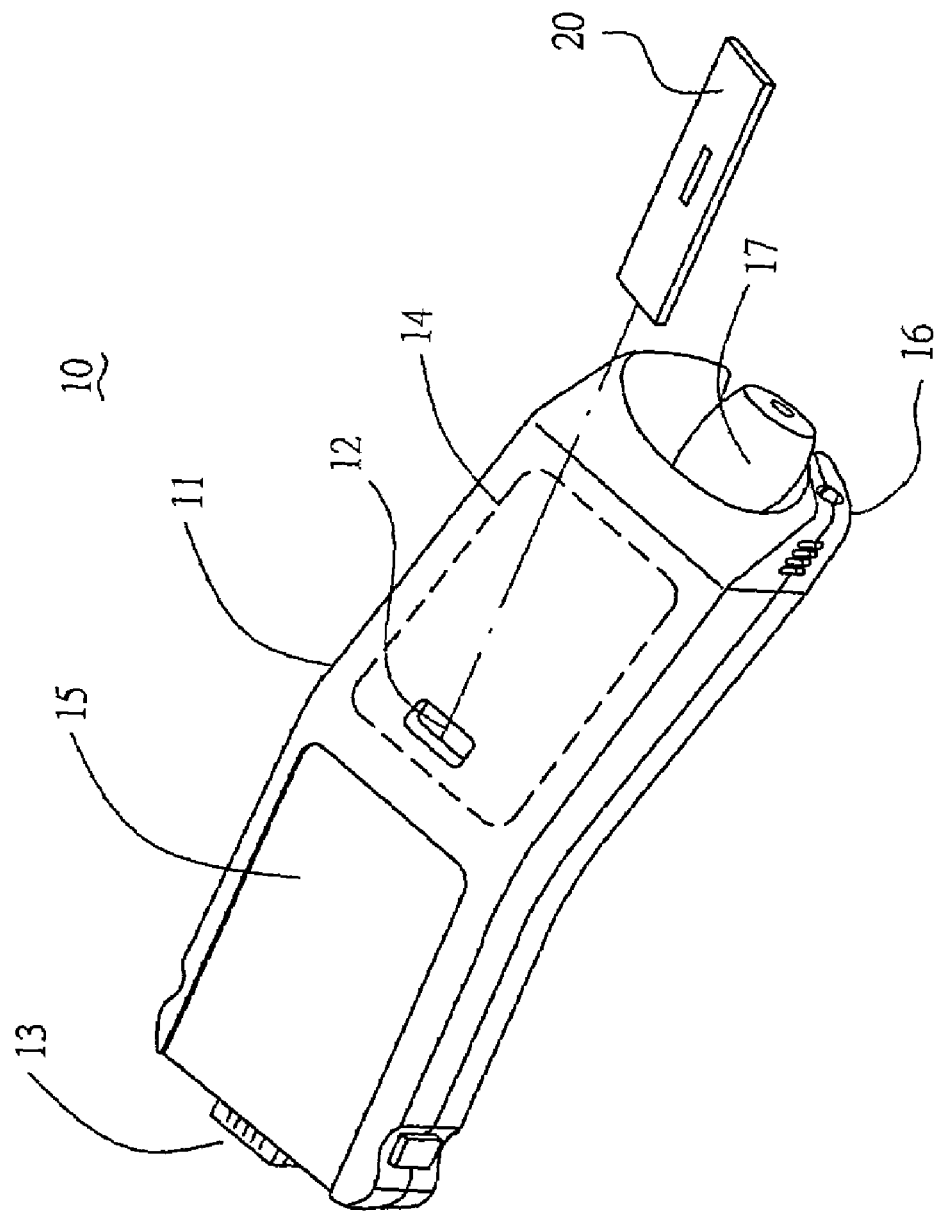
FIG. 1 is a schematic view of the biosensor monitor pursuant to the teachings of the present invention, illustrating the test strip to be inserted into the monitor.
Figure 2:
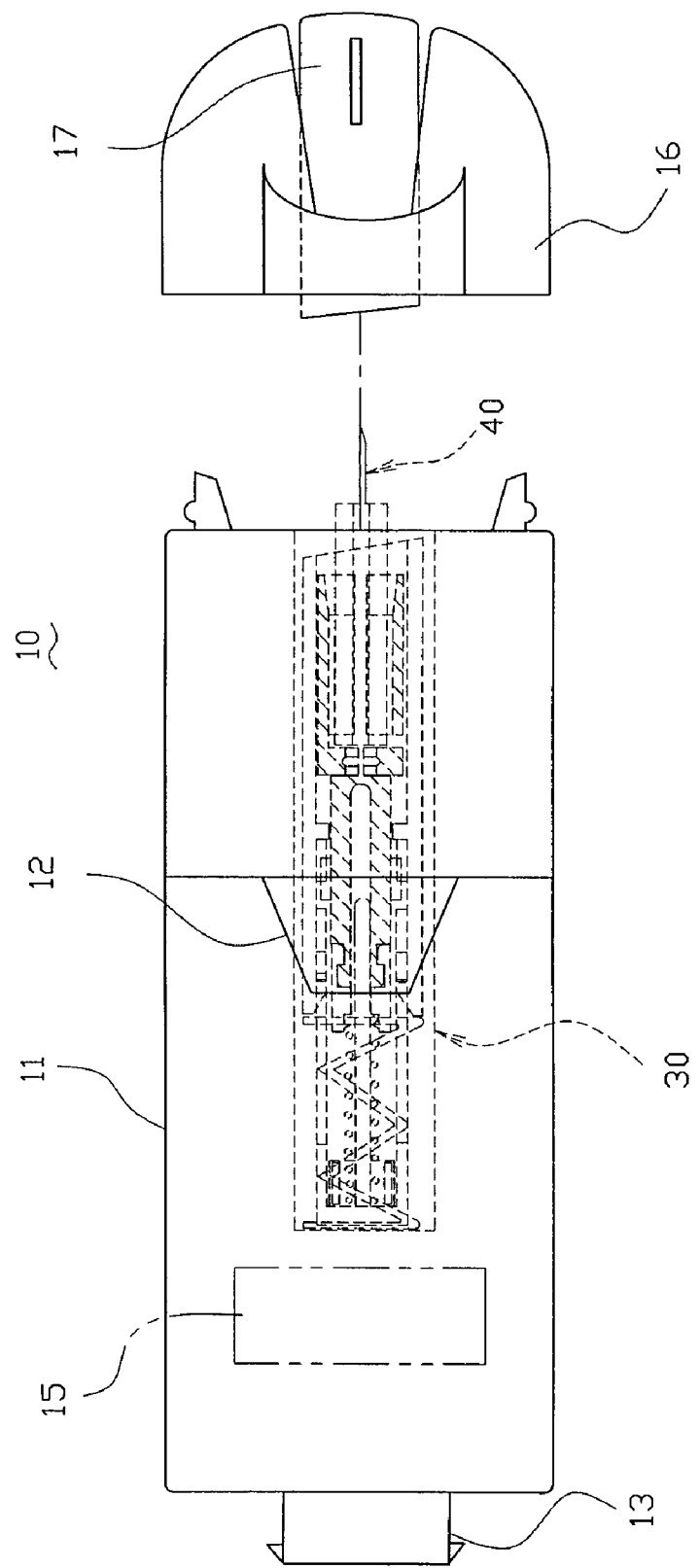
FIG. 2 illustrates the top view of the positional relationship of the several components of the biosensor monitor.
Figure 3:
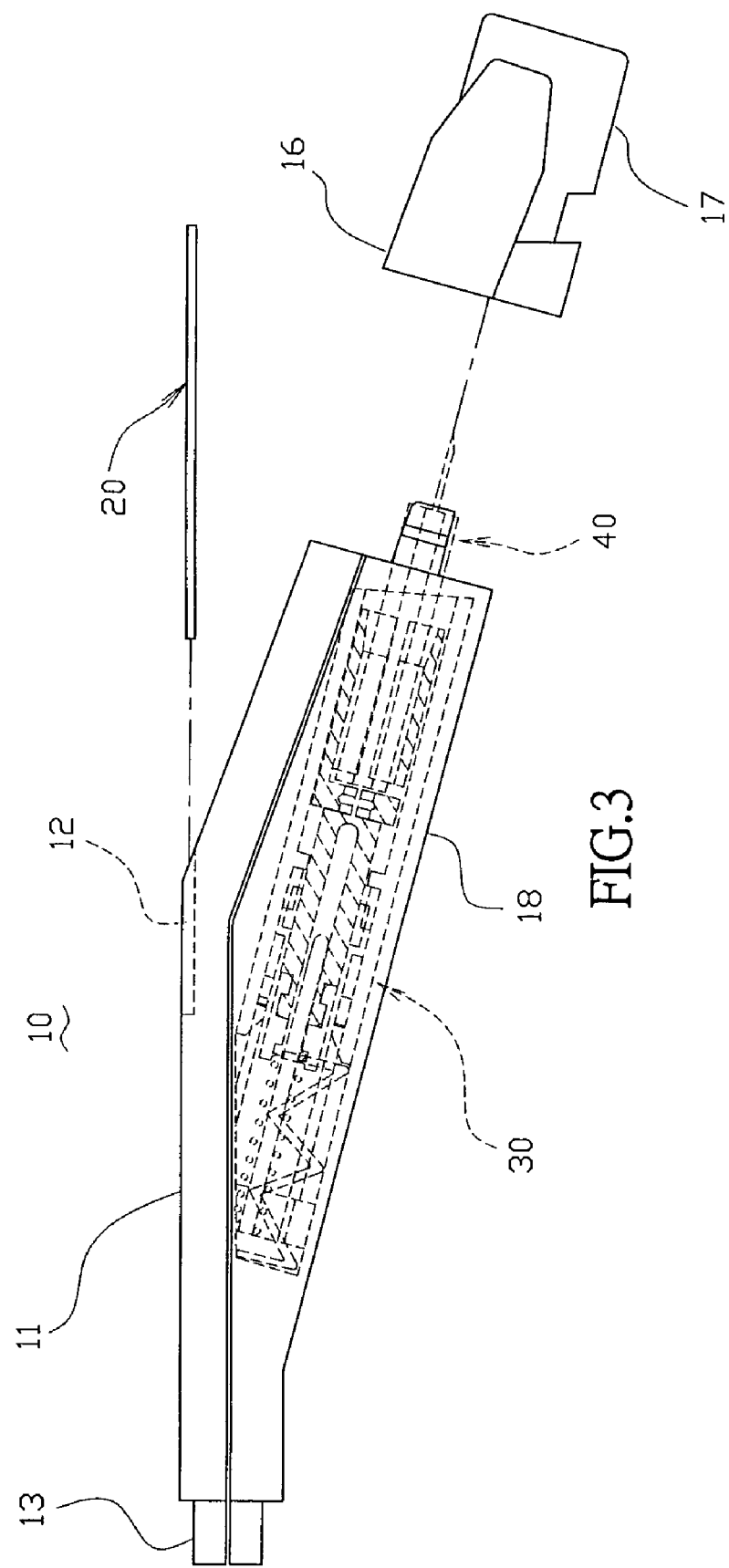
FIG. 3 illustrates the side view of the positional relationship of the several components of the biosensor monitors.

Referring to the drawings in detail, FIG. 1, the schematic view of the biosensor monitor pursuant to teachings of the present invention, shows a test strip 20 into the opening 12 on the upper protective cover 11 under which an electronic circuit board 14 is placed to measure the electrochemical response of the test strip with the added drop of blood, and on which a LCD screen 15 displays the results of the processed signals from the circuit board 14, and on which a communication port (USB, serial or parallel) 13 transmits the processed signals to the computer for data acquisition and analysis. Connected to this upper protective cover 11 is a protective cap 16 for the lancet, not shown, on which there sits a lancet cover 17. To have more insight into the mechanism of the monitor 10, FIG. 2 illustrates the positional relationship of the several components of the monitor. A number of components constitute the lancing device 30 situated inside the upper protective cover 11. A lancet 40 sits on the holder 35 in the lancing device 30. This FIG. 2 gives a better view of the lancet cover 17 and a protective cover 16 and the lancing device 30, while FIG. 3 gives the side cross sectional view of the monitor 10, the lancing device 30 and the protective cover 16 with the lancet cover 17.

Figure 7:
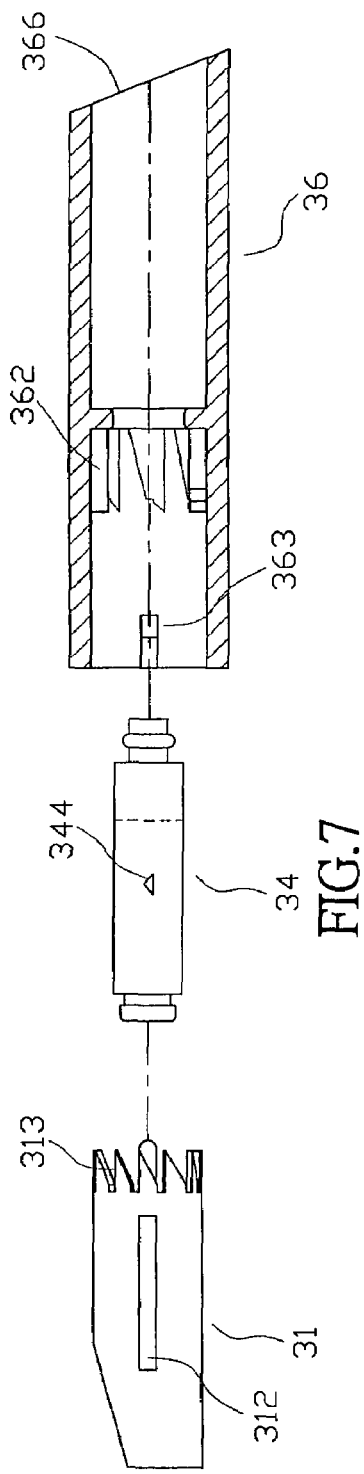
FIG. 7 illustrates the exploded view of some of the components of the lancing device.
Figure 8:
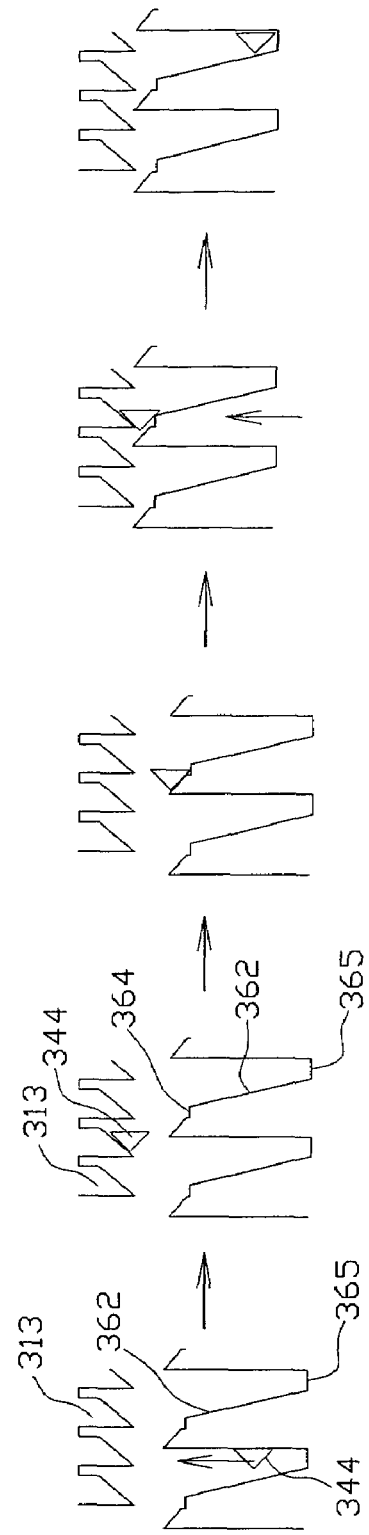
FIG. 8 illustrates the relative angular position of the two components of the lancing device.
Figure 9:
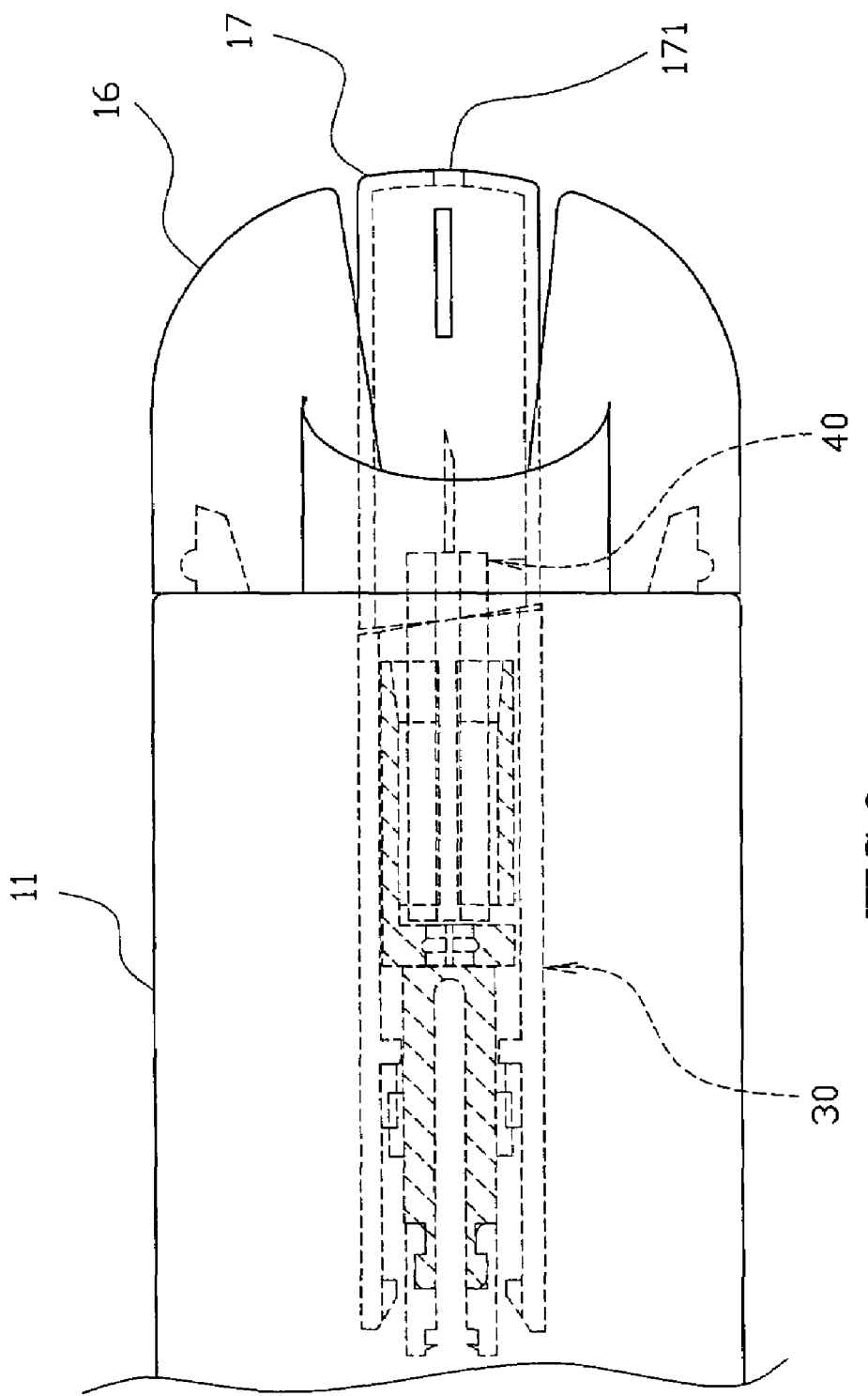
FIG. 9 is the top view of the positional relationship of the components of the monitor with the protective cap and lancet cover.

FIGS. 4, 5, and 6 illustrate the cross-sectional view of the lancing device 30 with the lancet 40 in three different operational modes. FIG. 4 shows the positional relationship of the components of the lancing device in the free relaxed state, wherein the spring 32 has neither compressive nor tensional stress. Whereas, FIG. 5 gives the positional relationship of the components of the lancing device 30 when the spring 32 is fully compressed to its limit as a lancet 40 is installed on, ready to release the lancet 40. As soon as the needle cover 17 is pressed by the slightly touch of a finger tip on the lancet cover 17, the lancet cover 17 will further push the outer tube 36 to the left to trigger the rotation of the connecting rod 34 which in turn trigger the release of the lancet holder 35 and the lancet 40 and other connecting components such as the connecting rod 34 and the adaptor 33, by the compressive force of the spring 32. The inner tube 31 is stationary and sits onto the lower protective cover 18 by the two posts 39 which fits into the opening space next to the left rear end of the inner tube 31, while the outer tube 36 slides along the inner tube 31, guided by the teeth 363, on the inner rim of the outer tube 36 which fits well into the opening slot 312 of the inner tube 31. The outer tube 36 can slide to the left by the push of the neighboring needle cover 17 to the right and can slide to the right position by the compressive force in the large spring 38. The sliding movement of the outer tube 36 only happens when the lancet 40 is ready for release. The inner tube 31 holds well to one end of the small spring 32, while the adaptor 33 locks well the other end of the small spring 32, and hence the adaptor 33 can not rotate. Although the adaptor 33 connects to the connecting rod 34, nevertheless, a good tolerance between them allows the connecting rod 34 to rotate freely against the adaptor 33. This connecting rod 34 engages with the lancet holder 35 and as they move to the left, the connecting rod 34 will rotate against the lancet holder 35 because the triangular protrusion 344 on the connection rod 34 will be guided to rotate by the teeth 313 of the inner tube 31, which can better be understood by referring to FIG. 7 and FIG. 8. The teeth 313 of the inner tube 31 will guide and force the triangular protrusion 344 of the connecting rod 34 to rotate relative to the inner tube 31, as the connecting rod 34 moves toward the inner tube 31, the teeth 362, which lies inside the inner wall of the outer tube 36, will further guide and force the triangular protrusion to rotate and stay either at the stop 364 or the extreme position 365, depending upon the relative position of the triangular protrusion 344 with the teeth 313. When the triangular protrusion stays at the location 364, the lancet holder 35 and the lancet 40 and the connecting rod 34 combination are in the position ready for the lancet 40 to launch for inoculation for blood, just like the mode in FIG. 5. Furthermore, when the triangular protrusion 344 stays at the location 365, the connecting rod 34 and the lancet 40 combinations are at the state of being after launch, just like the mode in FIG. 6. FIGS. 9, 10 and 11 illustrate the mechanism of the lancet cover 17 and the protective cover 16, with which the lancet cover 17 can rotate relative to the protective cover 16 to adjust the depth of the needle 40 piercing into the skin by the engaging slope 364 of the tube 36 with the slope 173 of the lancet cover 17, which has a hole 171 for the needle in front of the lancet 40 to go through and a number of grooves 172 for the protrusion 161 on the inner wall of the protective cover 16, as shown in FIGS. 10 and 11, to define the depth of lancet 40 into the skin, which then results in different amount of blood.

What is claimed is:

1. A biosensor monitor for use in measuring bioanalyte comprising:
   a) a test strip;
   b) a lancet;
   c) a lower protective cover;
   d) a lancing device having:
      i) an inner tube connected to the lower protective cover and having inner tube teeth;
      ii) a smaller spring;
      iii) a connecting rod inserted into an interior of the inner tube and having a protrusion, the smaller spring biasing the connecting rod outwardly from the interior of the inner tube, the inner tube teeth engaging with and forcing the connecting rod to rotate within the inner tube as the connector rod moves axially within the inner tube;
      iv) an adapter located between the smaller spring and the connecting rod, the adapter connecting the connecting rod to the smaller spring;
      v) a larger spring located around the inner tube;
      vi) an outer tube having an outer tube slope and outer tube teeth located on an inner wall thereof, the inner tube is partially inserted into an interior at a first end of the outer tube, the connecting rod, the adapter and the smaller spring are located in the interior of the outer tube, the protrusion of the connecting rod engaging the outer tube teeth and the inner tube teeth, the outer tube being pressed by the larger spring and selectively sliding toward the lancet cover and away from the inner tube, when a fingertip pushes on the lancet cover and hence the outer tube, the teeth on an inner rim of the outer tube forcing the protrusion of the connecting rod to rotate and trigger a release of the lancet holder, a lancet holder moving toward the fingertip; and
      vii) a lancet holder located in the interior of a second end of the outer tube and having a lancet cover slope, the lancet is located in the lancet holder, a lancet holder engaging with the connecting rod, the lancet holder sliding along the interior of the outer tube without rotating as the connecting rod rotates, outer tube slope of the outer tube engaging with the lancet cover slope on the lancet cover and selectively adjusting a depth of the lancet; and
   e) an upper protective cover connected to the lower protective cover and having:
      i) an electronic circuit board located on an interior thereof and analyzing an electrochemical reaction of the test strip with a bioanalyte;
      ii) an LCD monitor electrically connected to the electronic circuit board and displaying results from the electrochemical reaction of the test strip with the bioanalyte; and
      iii) an opening, the test strip is removably inserted into the opening, the lancing device is located in an end of the upper housing;
   f) a monitor cover having:
      i) a protective cap connected to the upper protective cover and the lower protective cover and having a hole and a protrusion located on an inner rim of the hole; and
      ii) a lancet cover located on an interior of the protective cap and having a plurality of grooves, a lancet cover slope, and a hole, the protrusion of the protective cap is located in a selected groove of the plurality of grooves, the lancet cover slope engaging the outer tube and selectively adjusting the depth of the lancet.

2. The biosensor monitor according to claim 1, further comprising a communication port located on the upper protective cover and the lower protective cover and electrically connected to the electronic circuit board.

* * * * *